(12) United States Patent
Oh et al.

(10) Patent No.: US 11,478,137 B2
(45) Date of Patent: Oct. 25, 2022

(54) CAPSULE ENDOSCOPE IMAGE RECEIVER AND CAPSULE ENDOSCOPE DEVICE HAVING THE SAME

(71) Applicant: ELECTRONICS AND TELECOMMUNICATIONS RESEARCH INSTITUTE, Daejeon (KR)

(72) Inventors: Kwang Il Oh, Daejeon (KR); Tae Wook Kang, Daejeon (KR); Sung Eun Kim, Daejeon (KR); Hyuk Kim, Daejeon (KR); Mi Jeong Park, Sejong (KR); Hyung-Il Park, Daejeon (KR); Kyung Jin Byun, Daejeon (KR); Jae-Jin Lee, Daejeon (KR); In Gi Lim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 394 days.

(21) Appl. No.: 16/842,497

(22) Filed: Apr. 7, 2020

(65) Prior Publication Data
US 2020/0315438 A1    Oct. 8, 2020

(30) Foreign Application Priority Data

Apr. 8, 2019  (KR) .................. 10-2019-0041095
Jul. 30, 2019  (KR) .................. 10-2019-0092449

(51) Int. Cl.
*A61B 1/04*       (2006.01)
*A61B 5/00*       (2006.01)
*A61B 1/00*       (2006.01)

(52) U.S. Cl.
CPC .......... *A61B 1/041* (2013.01); *A61B 1/00009* (2013.01); *A61B 5/0028* (2013.01); *A61B 5/0031* (2013.01)

(58) Field of Classification Search
CPC .. A61B 1/0028; A61B 1/00011; A61B 5/0028
See application file for complete search history.

(56) References Cited

U.S. PATENT DOCUMENTS 4,803,992 A * 2/1989 Lemelson ............ A61B 5/4839
                                                  600/561
5,113,869 A * 5/1992 Nappholz ............ A61B 5/0006
                                                  128/903
(Continued)

FOREIGN PATENT DOCUMENTS

JP      2012165384 A    8/2012
JP      2017147696 A    8/2017
(Continued)

*Primary Examiner* — John P Leubecker
*Assistant Examiner* — Jae Woo

(57) ABSTRACT

A capsule endoscope image receiver includes a receiving electrode unit that receives first and second differential signals from a capsule endoscope image transmitter through a human body communication channel, an analog amplifying unit that receives the first and second differential signals and outputs first and second amplified differential signals, and a signal restoring unit that receives the first and second amplified differential signals and restores image information. The analog amplifying unit includes a first amplifier that outputs the first amplified differential signal, a second amplifier that outputs the second amplified differential signal, and an input impedance that is connected between a first inverting input terminal of the first amplifier and a second inverting input terminal of the second amplifier and obtains a gain of differential signal amplification in which a high (Continued)

frequency component of the first and second amplified differential signals is greater than a low frequency component.

14 Claims, 10 Drawing Sheets

(56) References Cited

U.S. PATENT DOCUMENTS

| | | | | |
|---|---|---|---|---|
| 6,026,321 | A * | 2/2000 | Miyata | A61B 5/389 |
| | | | | 128/903 |
| 6,223,018 | B1 * | 4/2001 | Fukumoto | H04B 13/005 |
| | | | | 379/55.1 |
| 8,160,672 | B2 | 4/2012 | Kim et al. | |
| 8,554,312 | B2 * | 10/2013 | Pekonen | A61B 5/0245 |
| | | | | 600/509 |
| 8,781,562 | B2 * | 7/2014 | Pekonen | A61B 5/30 |
| | | | | 600/509 |
| 2002/0185999 | A1 * | 12/2002 | Tajima | H01Q 1/273 |
| | | | | 324/76.75 |
| 2005/0277844 | A1 * | 12/2005 | Strother | A61B 5/389 |
| | | | | 128/903 |
| 2006/0173265 | A1 * | 8/2006 | Kim | A61B 1/041 |
| | | | | 600/407 |
| 2007/0222033 | A1 | 9/2007 | Ariie et al. | |
| 2008/0180278 | A1 * | 7/2008 | Denison | A61B 5/7203 |
| | | | | 340/870.18 |
| 2010/0137708 | A1 * | 6/2010 | Tamura | A61B 5/053 |
| | | | | 600/424 |
| 2012/0143602 | A1 * | 6/2012 | Byun | G10L 19/06 |
| | | | | 704/219 |
| 2012/0201235 | A1 * | 8/2012 | Lim | H04B 13/005 |
| | | | | 370/349 |
| 2012/0262560 | A1 * | 10/2012 | Nisani | A61B 1/045 |
| | | | | 348/E7.085 |
| 2017/0241807 | A1 | 8/2017 | Hatakeyama et al. | |
| 2017/0367561 | A1 | 12/2017 | Park | |
| 2018/0026729 | A1 * | 1/2018 | Lim | A61B 1/00006 |
| | | | | 370/349 |
| 2018/0131230 | A1 * | 5/2018 | Müeller | A61B 1/00029 |
| 2018/0184980 | A1 * | 7/2018 | Qin | A61B 5/6843 |
| 2019/0076033 | A1 * | 3/2019 | Sweeney | A61B 5/02152 |
| 2019/0307318 | A1 * | 10/2019 | Oh | A61B 1/00009 |
| 2020/0232780 | A1 * | 7/2020 | Wu | G01B 7/287 |
| 2020/0294658 | A1 * | 9/2020 | Ohishi | A61B 5/1126 |
| 2020/0315438 | A1 * | 10/2020 | Oh | A61B 5/0028 |

FOREIGN PATENT DOCUMENTS

| | | |
|---|---|---|
| KR | 1020040068425 A | 7/2004 |
| KR | 101063859 B1 | 9/2011 |
| KR | 20120102201 A | 9/2012 |
| KR | 20180018922 A | 2/2018 |

* cited by examiner

CAPSULE ENDOSCOPE IMAGE RECEIVER AND CAPSULE ENDOSCOPE DEVICE HAVING THE SAME

CROSS-REFERENCE TO RELATED APPLICATIONS

This U.S. non-provisional patent application claims priority under 35 U.S.C. § 119 of Korean Patent Application Nos. 10-2019-0041095, filed on Apr. 8, 2019, and 10-2019-0092449, filed on Jul. 30, 2019, respectively, the entire contents of which are hereby incorporated by reference.

BACKGROUND

Embodiments of the inventive concept relate to an image signal processing, and more particularly, relate to a capsule endoscope image receiver and a capsule endoscope device including the capsule endoscope image receiver.

An endoscope is generally inserted into a body through the oral or anal cavities, and captures images of digestive walls along a digestive organ of the body to diagnose abnormal lesions that may occur on the digestive walls of the digestive organ. In general, a wired endoscope is used, and the wired endoscope has a limitation in that the reach is limited to a wire length. Accordingly, a capsule endoscope has been developed, which is capable of transmitting an image or video captured in the digestive organ to a receiving device that is attached to an outside of the body, using a wireless communication technology. The receiving device of the capsule endoscope records the transmitted image or video, and after the recording is completed, the image may be reconfirmed to determine whether there is abnormal lesions in the body.

Since the capsule endoscope transmits and receives a signal wirelessly, a diagnostic device may reach anywhere in the digestive organ in the body. Therefore, all paths through which food is moved may be photographed and recorded. In particular, a small intestine, which cannot be reached by a conventional wired endoscope, may also be photographed to diagnose abnormal lesions. Accordingly identification of diseases occurring in the small intestine may be made possible in advance by the capsule endoscopy.

SUMMARY

Embodiments according to the inventive concept provide a capsule endoscope image receiver and a capsule endoscope device including the same, which compensate for attenuation occurring in a signal transmission and reception process of a capsule endoscope device.

A capsule endoscope image receiver according to an embodiment of the inventive concept includes a receiving electrode unit that receives first and second differential signals from a capsule endoscope image transmitter through a human body communication channel, an analog amplifying unit that receives the first and second differential signals from the receiving electrode unit and outputs first and second amplified differential signals, based on the received first and second differential signals, and a signal restoring unit that receives the first and second amplified differential signals from the analog amplifying unit and restores image information, based on the received first and second amplified differential signals, and wherein the analog amplifying unit includes a first amplifier that outputs the first amplified differential signal, based on the first differential signal, a second amplifier that outputs the second amplified differential signal, based on the second differential signal, and an input impedance that is connected between a first inverting input terminal of the first amplifier and a second inverting input terminal of the second amplifier and obtains a gain of differential signal amplification in which a high frequency component of the first and second amplified differential signals is greater than a low frequency component.

According to an embodiment of the inventive concept, the input impedance may include an input resistor and an input capacitor that are connected in parallel between the first inverting input terminal and the second inverting input terminal.

According to an embodiment of the inventive concept, the analog amplifying unit may further include first and second feedback resistors, the first feedback resistor is connected between a first output terminal of the first amplifier and the first inverting input terminal, and the second feedback resistor is connected between a second output terminal of the second amplifier and the second inverting input terminal.

According to an embodiment of the inventive concept, a difference between the first and second amplified differential signals may have a magnitude amplified by the gain of the differential signal amplification than a difference between the first and second differential signals, and the gain of the differential signal amplification may be determined based on the first feedback resistor, the second feedback resistor, and the input impedance.

According to an embodiment of the inventive concept, the receiving electrode unit may include a first receiving electrode that receives the first differential signal and a second receiving electrode that receives the second differential signal, the first amplifier may receive the first differential signal from the first receiving electrode through a first amplifier coupling capacitor, and the second amplifier may receive the second differential signal from the second receiving electrode through a second amplifier coupling capacitor.

According to an embodiment of the inventive concept, the signal restoring unit may include a band pass filter that blocks noise of the first and second amplified differential signals that are received from the analog amplifying unit.

According to an embodiment of the inventive concept, the band pass filter may receive the first amplified differential signal from a first output terminal of the first amplifier through a first filter coupling capacitor, and the band pass filter may receive the second amplified differential signal from a second output terminal of the second amplifier through a second filter coupling capacitor.

According to an embodiment of the inventive concept, the signal restoring unit may include a digital restoring circuit that restores a data signal and a clock signal, based on the first and second amplified differential signals, the data signal may include the image information, and the clock signal may include clock signal information of the capsule endoscope image transmitter.

According to an embodiment of the inventive concept, the capsule endoscope image receiver may further include a digital receiving unit that receives the data signal and the clock signal from the digital restoring circuit and restores an image captured by the capsule endoscope image transmitter, based on the received data signal and the received clock signal.

According to an embodiment of the inventive concept, the signal restoring unit may further include a band pass filter that blocks noise of the first and second amplified differential signals received from the analog amplifying unit and outputs first and second filtered differential signals from which the noise is blocked, and a comparator that receives the first and second filtered differential signals and outputs a comparison signal restored to a size that the digital receiving unit is able to process to the digital restoring circuit, based on the received first and second filtered differential signals.

According to an embodiment of the inventive concept, the comparator may receive the first filtered differential signal from the band pass filter through a first comparator coupling capacitor and may receive the second filtered differential signal from the band pass filter through a second comparator coupling capacitor.

A capsule endoscope device according to an embodiment of the inventive concept includes a capsule endoscope image transmitter that captures an image of an inside of a body, obtains image information based on the captured image, and outputs first and second differential signals including the obtained image information, respectively, and a capsule endoscope image receiver, wherein the capsule endoscope image receiver includes, a receiving electrode unit that receives the first and second differential signals from the capsule endoscope image transmitter through a human body communication channel, an analog amplifying unit that receives the first and second differential signals from the receiving electrode unit and outputs first and second amplified differential signals, based on the received first and second differential signals, and a signal restoring unit that receives the first and second amplified differential signals from the analog amplifying unit and restores the image information, based on the received first and second amplified differential signals, and wherein the analog amplifying unit includes a first amplifier that outputs the first amplified differential signal, based on the first differential signal, a second amplifier that outputs the second amplified differential signal, based on the second differential signal, and an input impedance that is connected between a first inverting input terminal of the first amplifier and a second inverting input terminal of the second amplifier and that obtains a gain of differential signal amplification in which a high frequency component of the first and second amplified differential signals is greater than a low frequency component.

According to an embodiment of the inventive concept, the receiving electrode unit may include a first receiving electrode that receives the first differential signal and a second receiving electrode that receives the second differential signal, and wherein the capsule endoscope image transmitter may include an image sensor that captures the image inside the body and outputs an image signal including the obtained image information, a signal driver that receives the image signal from the image sensor and outputs the first and second differential signals, based on the image signal, a first transmitting electrode that receives the first differential signal from the signal driver and outputs the first differential signal to the first receiving electrode through the human body communication channel, and a second transmitting electrode that receives the second differential signal from the signal driver and outputs the second differential signal to the second receiving electrode through the human body communication channel.

According to an embodiment of the inventive concept, the first transmitting electrode may receive the first differential signal from the signal driver through a first current limitation resistor, and the second transmitting electrode may receive the second differential signal from the signal driver through a second current limitation resistor.

BRIEF DESCRIPTION OF THE FIGURES

The above and other objects and features of the inventive concept will become apparent by describing in detail exemplary embodiments thereof with reference to the accompanying drawings.

DETAILED DESCRIPTION

Hereinafter, embodiments of the inventive concept will be described clearly and in detail such that those skilled in the art may easily carry out the inventive concept.

Figure 1:
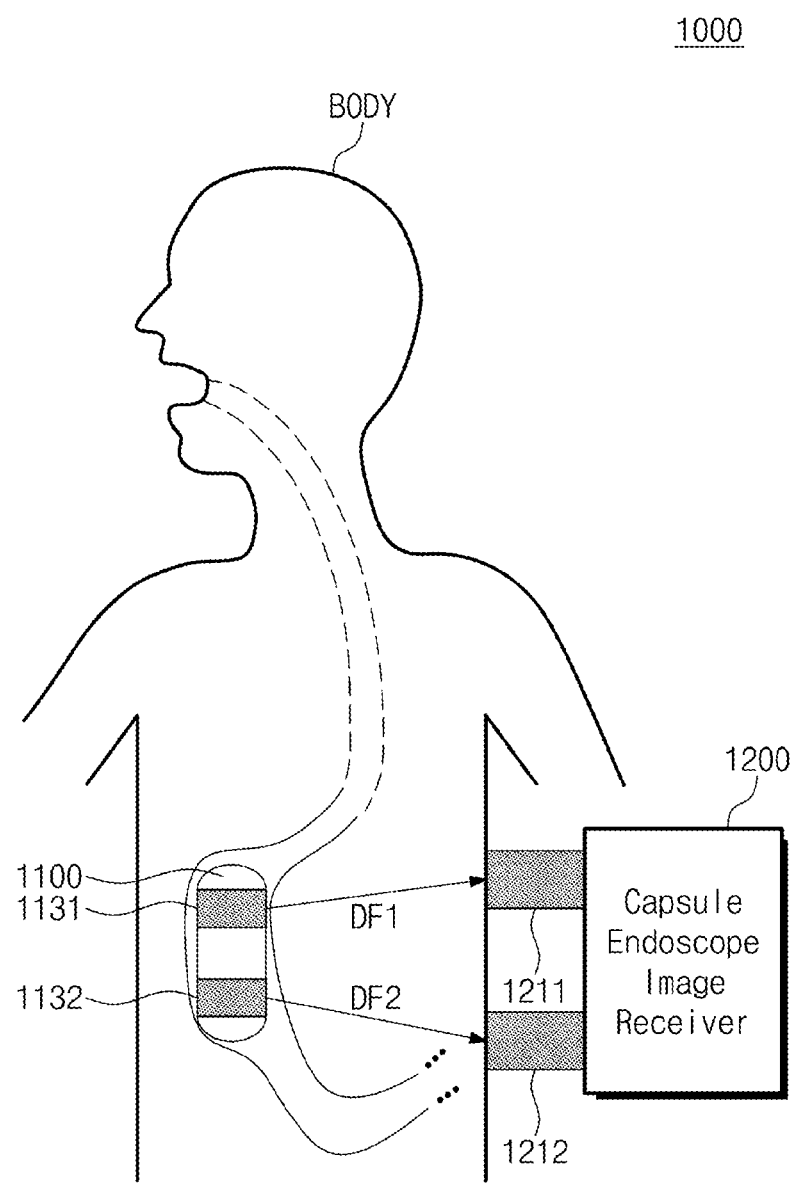
FIG. 1 is a diagram illustrating a capsule endoscope device according to an embodiment of the inventive concept.

FIG. 1 is a diagram illustrating a capsule endoscope device according to an embodiment of the inventive concept. Referring to FIG. 1, a capsule endoscope device 1000 may include a capsule endoscope image transmitter 1100 and a capsule endoscope image receiver 1200. The capsule endoscope device 1000 may obtain an image inside a body BODY.

The capsule endoscope image transmitter 1100 may include a first transmitting electrode 1131 and a second transmitting electrode 1132. The capsule endoscope image transmitter 1100 may capture an image inside the body BODY. Image information of a capsule endoscope may be obtained based on the captured image inside the body BODY.

The capsule endoscope image transmitter 1100 may output a first differential signal DF1 through the first transmitting electrode 1131. The capsule endoscope image transmitter 1100 may output a second differential signal DF2 through the second transmitting electrode 1132.

In this case, each of the first differential signal DF1 and the second differential signal DF2 may include the image information of the capsule endoscope. According to an embodiment of the inventive concept, the image information of the capsule endoscope may be transmitted based on a difference between the first differential signal DF1 and the second differential signal DF2.

That is, as the capsule endoscope image transmitter 1100 transmits the image information in a form of a differential signal, a wireless communication provided between the capsule endoscope image transmitter 1100 and the capsule endoscope image receiver 1200 is robust to noise and interference.

In an embodiment, the capsule endoscope image transmitter 1100 may be an ingestible sensor ingested into the mouth. For example, the capsule endoscope image transmitter 1100 may be a module having a pill form and a size that can be ingested through an oral cavity.

In an embodiment, the capsule endoscope image transmitter 1100 may capture a path and a digestive organ through which food is moving in the body BODY. Unlike when shooting with a wired endoscope, an examinee may take a daily life while shooting with the capsule endoscope.

The capsule endoscope image receiver 1200 may include at least one pair of receiving electrodes. Each of the at least one pair of receiving electrodes may include at least one first receiving electrode that receives the first differential signal DF1 and at least one second receiving electrode that receives the second differential signal DF2. For simplicity of drawing, a pair of receiving electrodes 1211 and 1212 are illustrated in FIG. 1, but the scope of the inventive concept is not limited thereto.

The capsule endoscope image receiver 1200 may receive the first differential signal DF1 through the first receiving electrode 1211. The capsule endoscope image receiver 1200 may receive the second differential signal DF2 through the second receiving electrode 1212. The capsule endoscope image receiver 1200 may restore the image inside the body BODY, based on the received differential signals DF1 and DF2.

According to an embodiment of the inventive concept, the first differential signal DF1 and the second differential signal DF2 that are output from the capsule endoscope image transmitter 1100 may be received to the capsule endoscope image receiver 1200 through a human body communication channel. The human body communication channel may be a communication channel using a part of the body BODY as a signal transmission medium. The human body communication channel may have a characteristic of a low pass filter (LPF) that passes a signal of a low frequency band and blocks a signal of a high frequency band.

Accordingly, each of the first differential signal DF1 and the second differential signal DF2 that are received by the capsule endoscope image receiver 1200 may be a signal in which an attenuation degree of component of the high frequency band is greater than an attenuation degree of component of a low frequency band. That is, the capsule endoscope image receiver 1200 may receive the first differential signal DF1 and the second differential signal DF2 in which the component of the high frequency band is attenuated.

Figure 2:
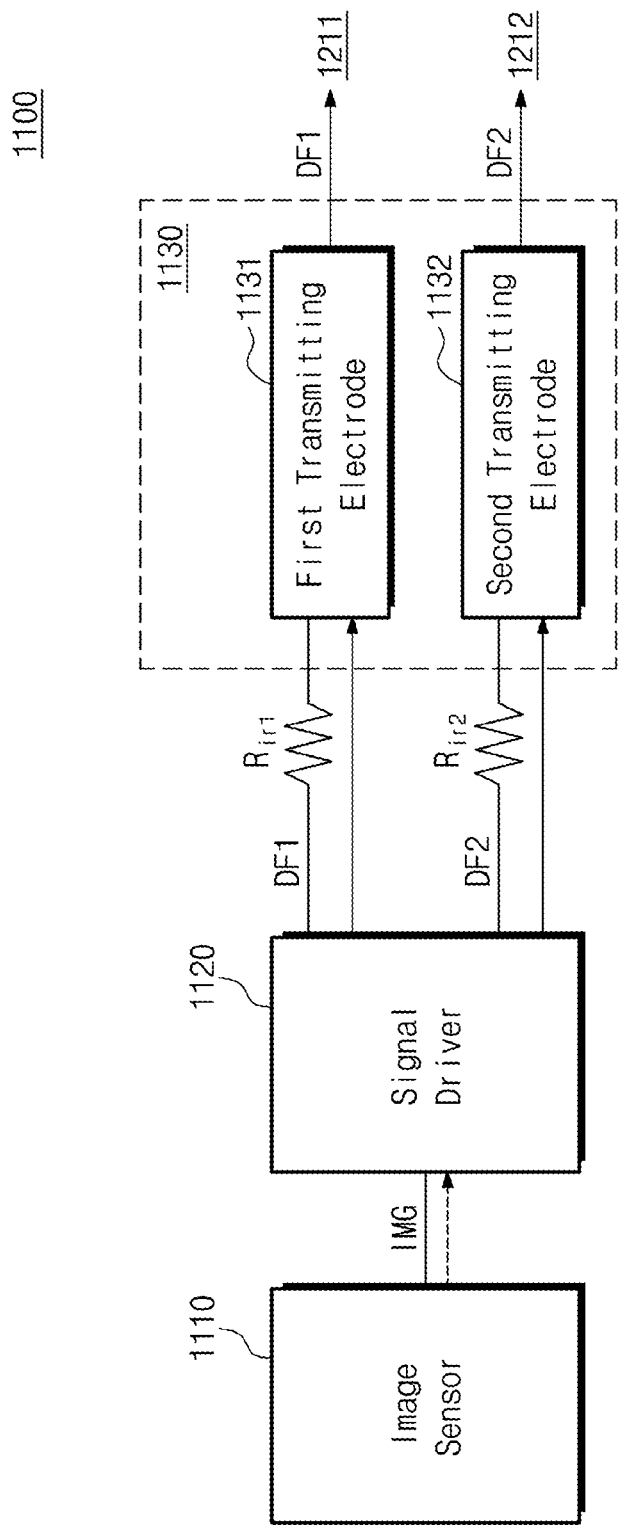
FIG. 2 is a diagram illustrating a capsule endoscope image transmitter of FIG. 1.

FIG. 2 is a diagram illustrating a capsule endoscope image transmitter of FIG. 1. Referring to FIG. 2, the capsule endoscope image transmitter 1100 may include an image sensor 1110, a signal driver 1120, and a transmitting electrode unit 1130. The capsule endoscope image transmitter 1100 may output the first differential signal DF1 and the second differential signal DF2 including the image information.

The image sensor 1110 may capture an image inside a body. The image sensor 1110 may obtain the image information, based on the captured image inside the body. The image sensor 1110 may output an image signal IMG including the image information.

The signal driver 1120 may receive the image signal IMG from the image sensor 1110. The signal driver 1120 may output the first differential signal DF1 and the second differential signal DF2, based on the received image signal IMG. Each of the differential signals DF1 and DF2 may include the image information. Each of the differential signals DF1 and DF2 may be a digital signal having a first voltage level or a second voltage level. The second voltage level may be greater than the first voltage level.

In an embodiment, the differential signals DF1 and DF2 that are output from the signal driver 1120 may be digital signals having a relatively short rising time and a relatively short falling time. In this case, the rising time may mean a time that is taken to rise from the first voltage level to the second voltage level. The falling time may mean a time that is taken to fall from the second voltage level to the first voltage level.

The digital signal having the short rising time and the short falling time may mean a signal in which an attenuation degree of component of the high frequency band is a relatively low. That is, the differential signals DF1 and DF2 that are output from the signal driver 1120 may be signals of which a magnitude of the component of the high frequency band and a magnitude of the component of the low frequency band are similar to each other.

The transmitting electrode unit 1130 may include the first transmitting electrode 1131 and the second transmitting electrode 1132. The first transmitting electrode 1131 may output the first differential signal DF1 received from the signal driver 1120. The second transmitting electrode 1132 may output the second differential signal DF2 received from the signal driver 1120.

In an embodiment, when the image signal IMG input to the signal driver 1120 has the second voltage level greater than the first voltage level, the signal driver 1120 may output a current to the first transmitting electrode 1131. The current eradiated from the first transmitting electrode 1131 may flow into the second transmitting electrode 1132 and the first receiving electrode 1211 through the human body communication channel. Accordingly, information associated with the image signal IMG having the second voltage level may be transferred to the capsule endoscope image receiver 1200.

In an embodiment, when the image signal IMG input to the signal driver 1120 has the first voltage level less than the second voltage level, the signal driver 1120 may output a current to the second transmitting electrode 1132. The current eradiated from the second transmitting electrode 1132 may flow into the first transmitting electrode 1131 and the second receiving electrode 1212 through the human body communication channel. Accordingly, information associated with the image signal IMG of the first voltage level may be transferred to the capsule endoscope image receiver 1200.

In an embodiment, a current limitation resistor may be connected between the signal driver 1120 and the transmitting electrode unit 1130. The current limitation resistor may be a resistor that is connected to prevent an excessive current from flowing through the body. For example, a first current limitation resistor $R_{ir1}$ may be connected between the signal driver 1120 and the first transmitting electrode 1131. The second current limitation resistor $R_{ir2}$ may be connected between the signal driver 1120 and the second transmitting electrode 1132.

That is, the first transmitting electrode 1131 may receive the first differential signal DF1 from the signal driver 1120 through the first current limitation resistor $R_{ir1}$. The second transmitting electrode 1132 may receive the second differential signal DF2 from the signal driver 1120 through the second current limitation resistor $R_{ir2}$.

In an embodiment, the differential signals DF1 and DF2 output from the transmitting electrode unit 1130 may be signals having increased rising time and increased falling time in a process of receiving the differential signals DF1 and DF2 from the signal driver 1120. The signal of which rising time and falling time are increased may be a signal in which an attenuation of the component of the high frequency band is greater than an attenuation of the component of the low frequency band. That is, the differential signals DF1 and DF2 output from the transmitting electrode unit 1130 may be signals having a magnitude of the component of the high frequency band is less than a magnitude of the component of the low frequency band.

Figure 3:
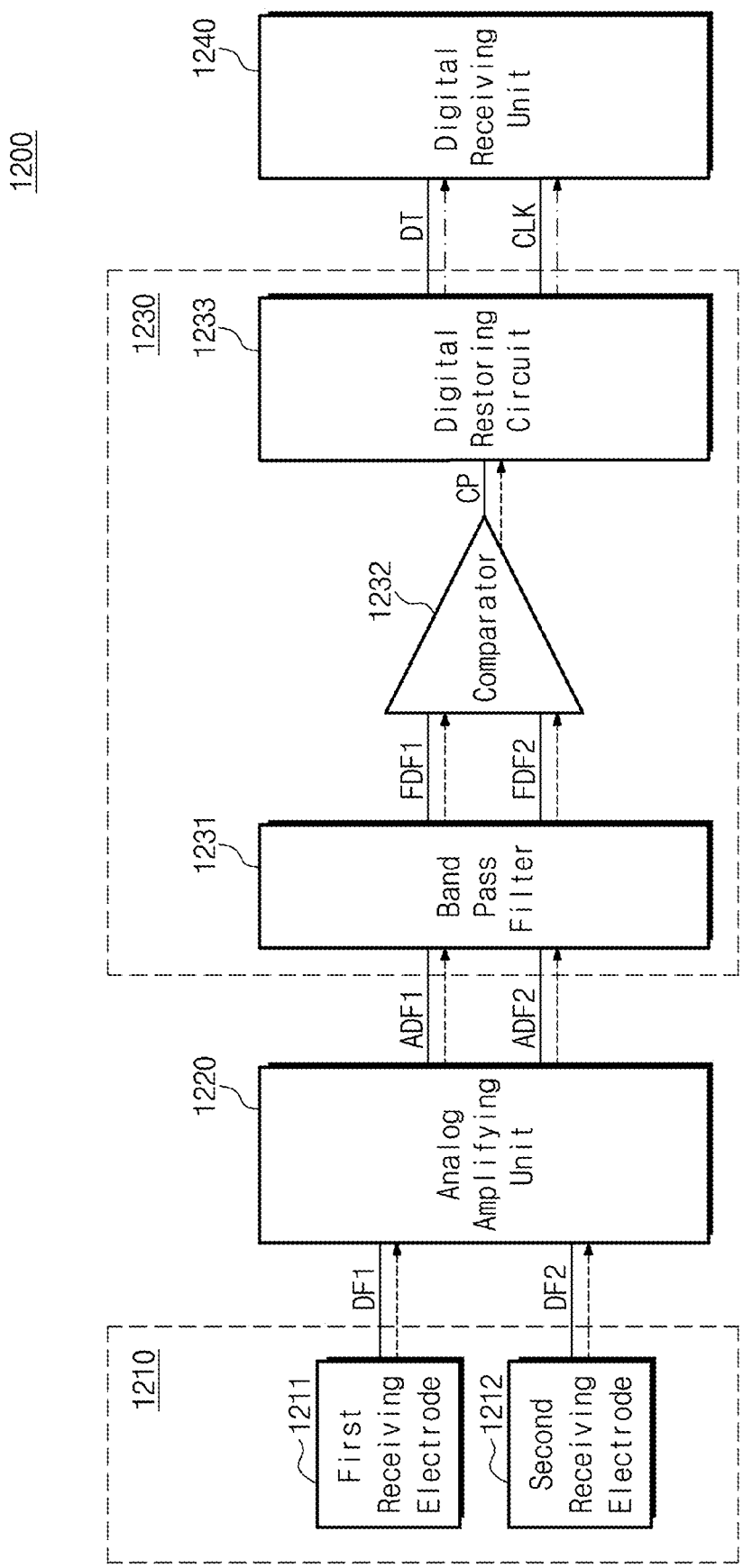
FIG. 3 is a diagram illustrating a capsule endoscope image receiver of FIG. 1.

FIG. 3 is a diagram illustrating a capsule endoscope image receiver of FIG. 1. Referring to FIG. 3, the capsule endoscope image receiver 1200 may include a receiving electrode unit 1210, an analog amplifying unit 1220, a signal restoring unit 1230, and a digital receiving unit 1240. The capsule endoscope image receiver 1200 may restore an image inside the body, based on the received differential signals DF1 and DF2.

The receiving electrode unit 1210 may include at least a pair of receiving electrodes. In more detail, the receiving electrode unit 1210 may include at least one first receiving electrode that transfers the first differential signal DF1 received from the first transmitting electrode 1131 to the analog amplifying unit 1220. The receiving electrode unit 1210 may include at least one second receiving electrode that transfers the second differential signal DF2 received from the second transmitting electrode 1132 to the analog amplifying unit 1220. To provide a thorough understanding of the inventive concept, although the receiving electrode unit 1210 including the pair of receiving electrodes is illustrated in FIG. 3, the scope of the inventive concept is not limited thereto.

In an embodiment, the receiving electrode unit 1210 may include the first receiving electrode 1211 and the second receiving electrode 1212. The first receiving electrode 1211 may receive the first differential signal DF1 output from the first transmitting electrode 1131 through the human body communication channel. The second receiving electrode 1212 may receive the second differential signal DF2 output from the second transmitting electrode 1132 through the human body communication channel. The received differential signals DF1 and DF2 may be signals in which the component of the high frequency band is attenuated.

The analog amplifying unit 1220 may receive the first differential signal DF1 through the first receiving electrode 1211. The analog amplifying unit 1220 may receive the second differential signal DF2 through the second receiving electrode 1212. The analog amplifying unit 1220 may output a first amplified differential signal ADF1 by amplifying the received first differential signal DF1. The analog amplifying unit 1220 may output a second amplified differential signal ADF2 by amplifying the received second differential signal DF2.

The analog amplifying unit 1220 may be a module that amplifies the differential signals DF1 and DF2 received from the receiving electrode unit 1210 with a gain of differential signal amplification. The gain of the differential signal amplification may mean a value obtained by dividing a difference between the amplified differential signals ADF1 and ADF2 by a difference between the differential signals DF1 and DF2.

In an embodiment, the analog amplifying unit 1220 may include an input resistor and a feedback resistor. The gain of the differential signal amplification may be determined based on a ratio between the input resistance and the feedback resistance.

In an embodiment, the analog amplifying unit 1220 may be a module in which the gain of the differential signal amplification at the high frequency band and the gain of the differential signal amplification at the low frequency band are similar to each other. In this case, the gain of the differential signal amplification may be expressed by an equation having no zero at a frequency domain. That is, each of the differential signals ADF1 and ADF2 amplified by the analog amplifying unit 1220 may be a signal of which a magnitude of the component of the high frequency band is less than a magnitude of the component of the low frequency band.

The signal restoring unit 1230 may include a band pass filter 1231, a comparator 1232, and a digital restoring circuit 1233. The signal restoring unit 1230 may receive the differential signals ADF1 and ADF2 amplified from the analog amplifying unit 1220. The signal restoring unit 1230 may be a module that restores a data signal DT and a clock signal CLK, based on the amplified differential signals ADF1 and ADF2.

In this case, the data signal DT may be a digital signal in which an image signal generated by the capsule endoscope image transmitter 1100 is restored. The clock signal CLK may be a signal from which a clock signal used in the capsule endoscope image transmitter 1100 is restored. That is, the data signal DT may be a signal including image information inside the body. The signal restoring unit 1230 may restore image information inside the body. The clock signal CLK may include information associated with the clock signal in the capsule endoscope image transmitter 1100.

The band pass filter 1231 may receive the amplified differential signals ADF1 and ADF2 from the analog amplifying unit 1220. The band pass filter 1231 may output a first filtered differential signal FDF1 and a second filtered differential signal FDF2.

In this case, the first filtered differential signal FDF1 may be a signal from which noise is blocked in the first amplified differential signal ADF1. The second filtered differential signal FDF2 may be a signal from which noise is blocked in the second amplified differential signal ADF2. That is, the band pass filter 1231 may be a band pass filter (BPF) that blocks noise of the amplified differential signals ADF1 and ADF2.

The comparator 1232 may receive the filtered differential signals FDF1 and FDF2 from the band pass filter 1231. The comparator 1232 may output a comparison signal CP. The comparison signal CP may be a signal in which the filtered differential signals FDF1 and FDF2 are restored to a magnitude of a digital signal that may be processed by the digital receiving unit 1240. That is, the comparator 1232 may be a module that restores a magnitude of the filtered differential signals FDF1 and FDF2 to the magnitude of the digital signal that may be processed by the digital receiving unit 1240, and transfers the restored signals to the digital restoring circuit 1233.

The digital restoring circuit 1233 may receive the comparison signal CP from the comparator 1232. The digital restoring circuit 1233 may output the data signal DT and the clock signal CLK to the digital receiving unit 1240. The data signal DT and the clock signal CLK may be signals restored from the comparison signal CP. That is, the digital restoring circuit 1233 may be a circuit that restores the data signal DT and the clock signal CLK from the comparison signal CP.

The digital receiving unit 1240 may receive the data signal DT and the clock signal CLK from the digital restoring circuit 1233. The digital receiving unit 1240 may restore the image inside the body, based on the received data signal DT and the clock signal CLK. The image inside the body restored by the digital receiving unit 1240 may be a distorted image due to attenuation generated in a process of modulation to the digital signal and attenuation generated through the human body communication channel.

As described above, according to an embodiment of the inventive concept, the capsule endoscope image receiver 1200 including the analog amplifying unit 1220 in which the gain of the differential signal amplification at the high frequency band is similar to the gain of the differential signal amplification at the low frequency band may be provided. In this case, each of the amplified differential signals FDF1 and FDF2 output from the analog amplifying unit 1220 may be a signal of which a magnitude of the high frequency component is less than a magnitude of the low frequency component.

Figure 4:
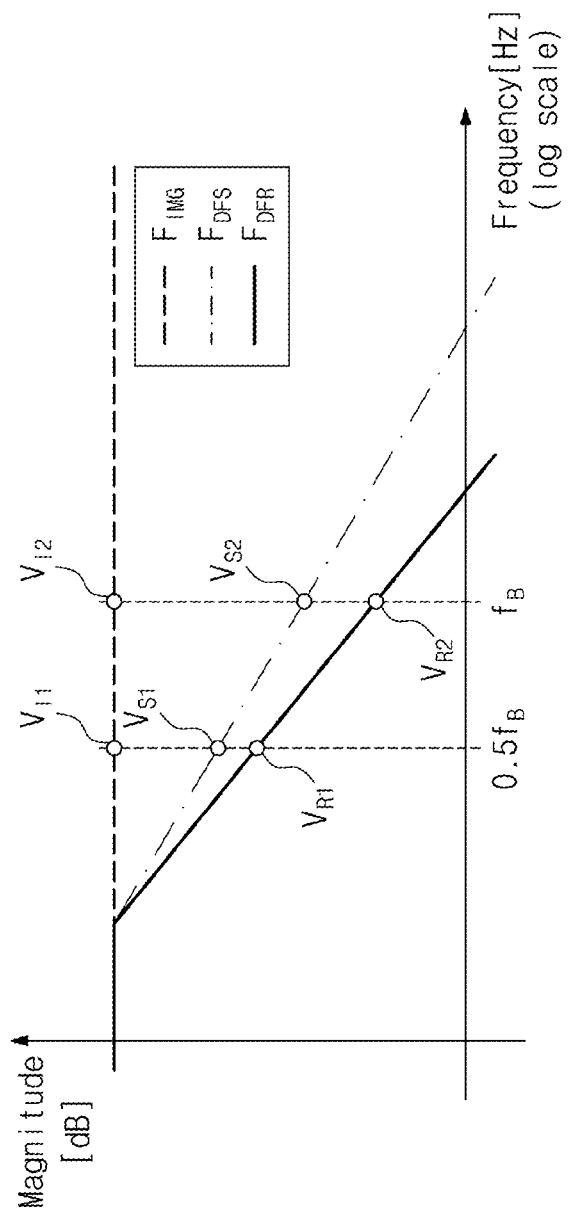
FIG. 4 is a graph illustrating signals of a capsule endoscope device including a capsule endoscope image receiver of FIG. 3 in a frequency domain.

FIG. 4 is a graph illustrating signals of a capsule endoscope device including a capsule endoscope image receiver of FIG. 3 in a frequency domain. Referring to FIG. 4, an image signal frequency waveform $F_{-IMG}$, a transmitting differential signal frequency waveform $F_{DFS}$, and a receiving differential signal frequency waveform $F_{DFR}$ are illustrated in the frequency domain.

The image signal frequency waveform $F_{-IMG}$ is a waveform illustrating a magnitude of a voltage of the image signal $F_{-IMG}$ that is output from the image sensor 1110 of the capsule endoscope image transmitter 1100 of FIG. 2 in the frequency domain. The image signal frequency waveform $F_{-IMG}$ is depicted by a dashed line.

Referring to the image signal frequency waveform $F_{-IMG}$, a magnitude $V_{I1}$ of a first image voltage may be a magnitude of a frequency 0.5 $f_B$ component that is half of a baseband frequency in the image signal IMG. A magnitude $V_{I2}$ of a second image voltage may be a magnitude of a baseband frequency $f_B$ component in the image signal IMG.

In an embodiment, the magnitude of the high frequency band component and the magnitude of the low frequency band component in the image signal IMG may be similar to each other. For example, the magnitude $V_{I1}$ of the first image voltage may be similar to the magnitude $V_{I2}$ of the second image voltage.

The transmitting differential signal frequency waveform $F_{DFS}$ is a waveform illustrating a magnitude of a difference between the differential signals DF1 and DF2 that are output from the transmitting electrode unit 1130 of the capsule endoscope image transmitter 1100 of FIG. 2, in the frequency domain. The transmitting differential signal frequency waveform $F_{DFS}$ is depicted by a dash-single dotted line.

As described above, a gain may be attenuated while the differential signal is transmitted through the human body communication channel. For a better understanding of the inventive concept, the differential signal output from the transmitting electrode unit 1130 and the differential signal input to the receiving electrode unit 1210 will be described separately. That is, the differential signal output from the transmitting electrode unit is described in the transmitting differential signal frequency waveform $F_{DFS}$, and the differential signal input to the receiving electrode unit will be described in the receiving differential signal frequency waveform $F_{DFR}$.

Referring to the transmitting differential signal frequency waveform $F_{DFS}$, a magnitude $V_{S1}$ of a first transmitting voltage may be a magnitude of a difference between the differential signals DF1 and DF2 at a frequency 0.5 $f_B$ component that is half of a baseband frequency in the transmitting electrode unit. A magnitude $V_{S2}$ of a second transmission voltage may be a magnitude of a difference between the differential signals DF1 and DF2 at the baseband frequency $f_B$ component in the transmitting electrode unit.

In an embodiment, as the rising time and the falling time are increased in the process of receiving the differential signals DF1 and DF2 from the signal driver 1120, the differential signals DF1 and DF2 that are output from the transmitting electrode unit 1130 may be signals in which a high frequency component is attenuated.

In this case, a difference between the differential signals of the high frequency component in the transmitting electrode unit may be more attenuated than a difference between the differential signals of the low frequency component. For example, the difference between the magnitude $V_{I2}$ of the second image voltage and the magnitude $V_{S2}$ of the second transmitting voltage may be greater than the difference between the magnitude $V_{I1}$ of the first image voltage and the magnitude $V_{S1}$ of the first transmitting voltage.

The receiving differential signal frequency waveform $F_{DFR}$ is a waveform illustrating a magnitude of a difference between the differential signals DF1 and DF2 that are input to the receiving electrode unit 1210 of the capsule endoscope image receiver 1200 of FIG. 3, in the frequency domain. The receiving differential signal frequency waveform $F_{DFR}$ is depicted by a solid line.

Referring to the receiving differential signal frequency waveform $F_{DFR}$, a magnitude $V_{R1}$ of a first receiving voltage may be a magnitude of a difference between the differential signals DF1 and DF2 at a frequency 0.5 $f_B$ component that is half of a baseband frequency in the receiving electrode unit. A magnitude $V_{R2}$ of a second receiving voltage may be a magnitude of a difference between the differential signals DF1 and DF2 at the baseband frequency $f_B$ component in the receiving electrode unit.

In an embodiment, as each of the differential signals DF1 and DF2 is attenuated while the differential signals DF1 and DF2 are transmitted through the human body communication channel having a low pass characteristic, the difference between the differential signals of the high frequency component may be attenuated more than the difference between the differential signals of the low frequency component in the receiving electrode unit. For example, the difference between the magnitude $V_{S2}$ of the second transmitting voltage and the magnitude $V_{R2}$ of the second receiving voltage may be greater than the difference between the magnitude $V_{S1}$ of the first transmitting voltage and the magnitude $V_{R1}$ of the first receiving voltage.

Figure 5:
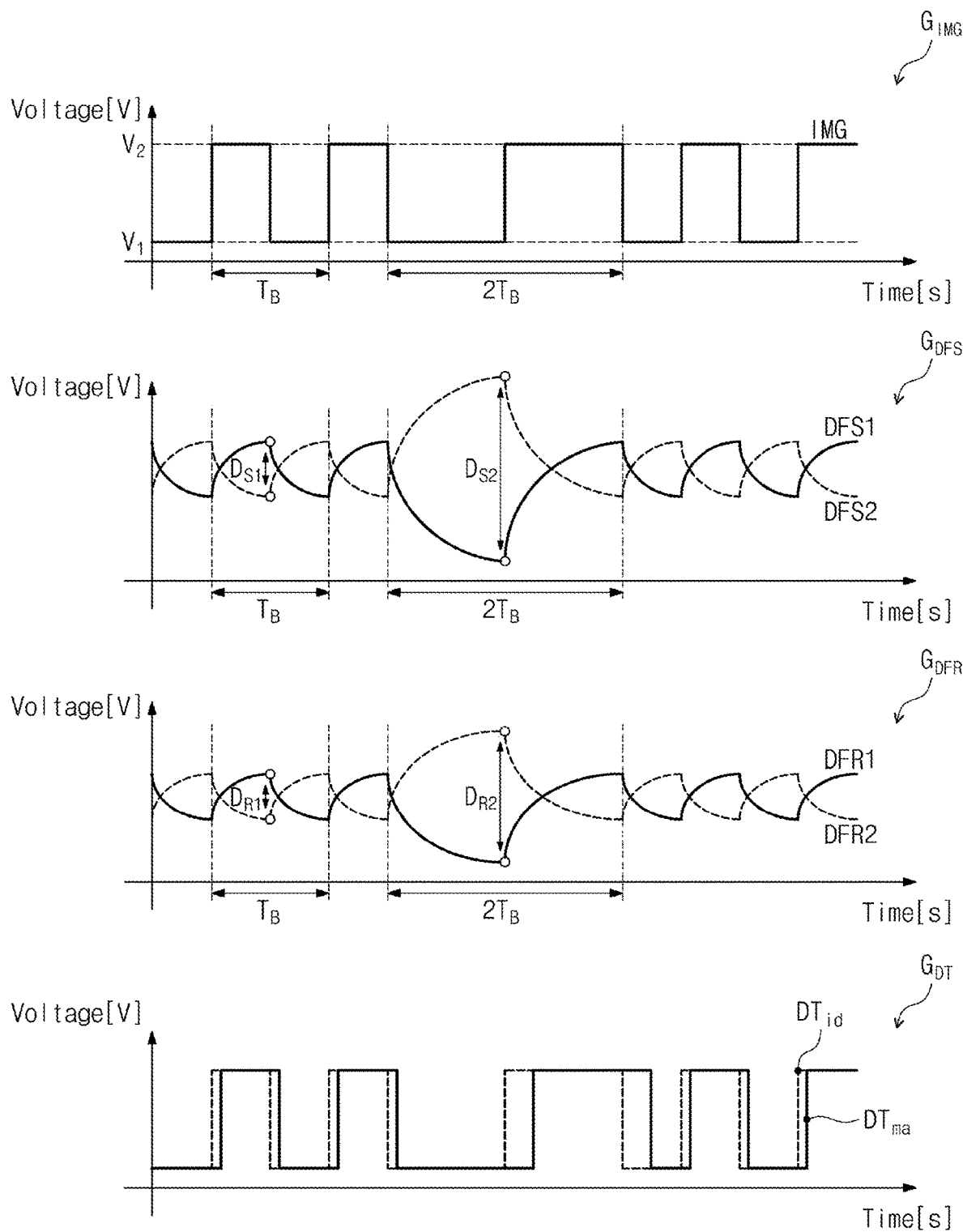
FIG. 5 is a graph illustrating signals of a capsule endoscope device including a capsule endoscope image receiver of FIG. 3 in a time domain.

FIG. 5 is a graph illustrating signals of a capsule endoscope device including a capsule endoscope image receiver of FIG. 3 in a time domain. Referring to FIG. 5, an image signal graph $G_{IMG}$, a transmitting differential signal graph $G_{DFS}$, a receiving differential signal graph $G_{DFR}$, and a data signal graph $G_{DT}$ are illustrated.

The image signal graph $G_{IMG}$ illustrates a voltage of the image signal IMG that is output from the image sensor 1110 of the capsule endoscope image transmitter 1100 of FIG. 2 in the time domain.

The image signal IMG may be a signal that periodically toggles. The toggle may mean that a voltage level of a specific signal changes. For example, toggling of the image signal IMG may mean that a value of the image signal IMG is changed from a first voltage level $V_1$ to a second voltage level $V_2$, or from the second voltage level $V_2$ to the first voltage level $V_1$.

In an embodiment, the image signal IMG may be a signal that toggles every bit, which is a minimum unit of information. In this case, the image signal IMG may include the baseband frequency $f_B$ component. The image signal IMG may include a frequency 0.5 $f_B$ component that is half of the baseband frequency that toggles after successive "2" bits.

Since a period is an inverse of a frequency, the image signal IMG may have a waveform of a baseband period $T_B$ corresponding to the baseband frequency $f_B$ component. In addition, the image signal IMG may have a waveform of a period 2 $T_B$ of "2" times the baseband period corresponding to a frequency 0.5 $f_B$ component that is half of the baseband frequency. That is, the image signal IMG may include a component of the baseband period $T_B$ and a component of the period 2 $T_B$ of "2" times the baseband period.

The transmitting differential signal graph $G_{DFS}$ illustrates the voltage of the differential signals DF1 and DF2 that are output from the transmitting electrode unit 1130 of the capsule endoscope image transmitter 1100 of FIG. 2 in the time domain. The differential signals DF1 and DF2 that are output from the transmitting electrode unit 1130 may be signals attenuated due to an increase of the rising time and the falling time.

In the transmitting differential signal graph $G_{DFS}$, a first transmitting differential signal DFS1 may be the first differential signal DF1 that is output from the transmitting electrode unit 1130. The first transmitting differential signal DFS1 is depicted by a solid line. A second transmitting differential signal DFS2 may be the second differential signal DF2 that is output from the transmitting electrode unit 1130. The second transmitting differential signal DFS2 is depicted by a dashed line.

In an embodiment, each of the transmitting differential signals DFS1 and DFS2 may include a component of the baseband period $T_B$. A first transmitting voltage difference $D_{S1}$ may be a voltage difference having a maximum magnitude among voltage differences between the transmitting differential signals DFS1 and DFS2 in a component of the baseband period $T_B$.

In an embodiment, each of the transmitting differential signals DFS1 and DFS2 may include a component of a period 2 $T_B$ of "2" times the baseband period. A second transmitting voltage difference DS2 may be a voltage difference having a maximum magnitude among voltage differences between the transmitting differential signals DFS1 and DFS2 in the component of the period 2 $T_B$ of "2" times the baseband period.

In an embodiment, the voltage difference between the transmitting differential signals DFS1 and DFS2 may be greater in attenuation in the high frequency component than in the low frequency component. That is, a magnitude of the voltage difference of the high frequency component may be less than a magnitude of the voltage difference of the low frequency component. For example, the first transmitting voltage difference $D_{S1}$ may be smaller than the second transmitting voltage difference $D_{S2}$.

The receiving differential signal graph $G_{DFR}$ illustrates the voltage of the differential signals DF1 and DF2 that are input to the receiving electrode unit 1210 of the capsule endoscope image receiver 1200 of FIG. 3 in the time domain. The differential signals DF1 and DF2 input to the receiving electrode unit 1210 may be signals attenuated due to being transmitted through the human body communication channel.

In the receiving differential signal graph $G_{DFR}$, a first receiving differential signal DFR1 may be the first differential signal DF1 input to the receiving electrode unit 1210. The first receiving differential signal DFR1 is depicted by a solid line. A second receiving differential signal DFR2 may be the second differential signal DF2 input to the receiving electrode unit 1210. The second receiving differential signal DFR2 is depicted by a dashed line.

In an embodiment, each of the receiving differential signals DFR1 and DFR2 may include a component of the baseband period $T_B$. A first receiving voltage difference $D_{R1}$ may be a voltage difference that is a maximum magnitude of the voltage differences between the receiving differential signals DFR1 and DFR2 in the component of the baseband period $T_B$.

In an embodiment, each of the receiving differential signals DFR1 and DFR2 may include a component of a period 2 $T_B$ of "2" times the baseband period. The second receiving voltage difference $D_{R2}$ may be a voltage difference that is a maximum magnitude of the voltage differences between the receiving differential signals DFR1 and DFR2 in the component of the period 2 $T_B$ that is "2" times the baseband period.

In an embodiment, the voltage difference between the receiving differential signals DFR1 and DFR2 may show that the attenuation in the high frequency component is greater than that of the low frequency component. For example, the first transmitting voltage difference $D_{S1}$ may be less than the second transmitting voltage difference $D_{S2}$. The value obtained by subtracting the first receiving voltage difference $D_{R1}$ from the first transmitting voltage difference $D_{S1}$ may be greater than the value obtained by subtracting the second receiving voltage difference $D_{R2}$ from the second transmitting voltage difference $D_{S2}$. Accordingly, the first receiving voltage difference $D_{R1}$ may be less than the second receiving voltage difference $D_{R2}$.

The data signal graph $G_{DT}$ illustrates a data signal $DT_{ma}$ that is output from the digital restoring circuit 1233 of the capsule endoscope image receiver 1200 of FIG. 3 and an ideal data signal $DT_{id}$ in the time domain. In this case, the ideal data signal $DT_{id}$ may be similar to the image signal IMG illustrated in the image signal graph $G_{IMG}$.

In an embodiment, the data signal $DT_{ma}$ according to an embodiment of FIG. 3 may be a signal in which a bit error occurs as the high frequency component is attenuated. For example, the data signal $DT_{ma}$ according to an embodiment of FIG. 3 may have a bit width different from the ideal data signal $DT_{id}$.

In an embodiment, the image inside the body, which is restored based on a data signal (e.g., $DT_{ma}$) having a bit width different from the ideal data signal $DT_{id}$, may be an image having a deteriorated image quality.

As described above, according to an embodiment of the inventive concept, the high frequency component of the differential signal may be attenuated due to the increase of the rising time and the falling time. As the differential signal is transmitted through the human body communication channel, the high frequency component may be attenuated. A restored data signal (e.g., $DT_{ma}$) based on the differential signal in which the high frequency component is attenuated may be a signal in which a bit width variation is generated.

Figure 6:
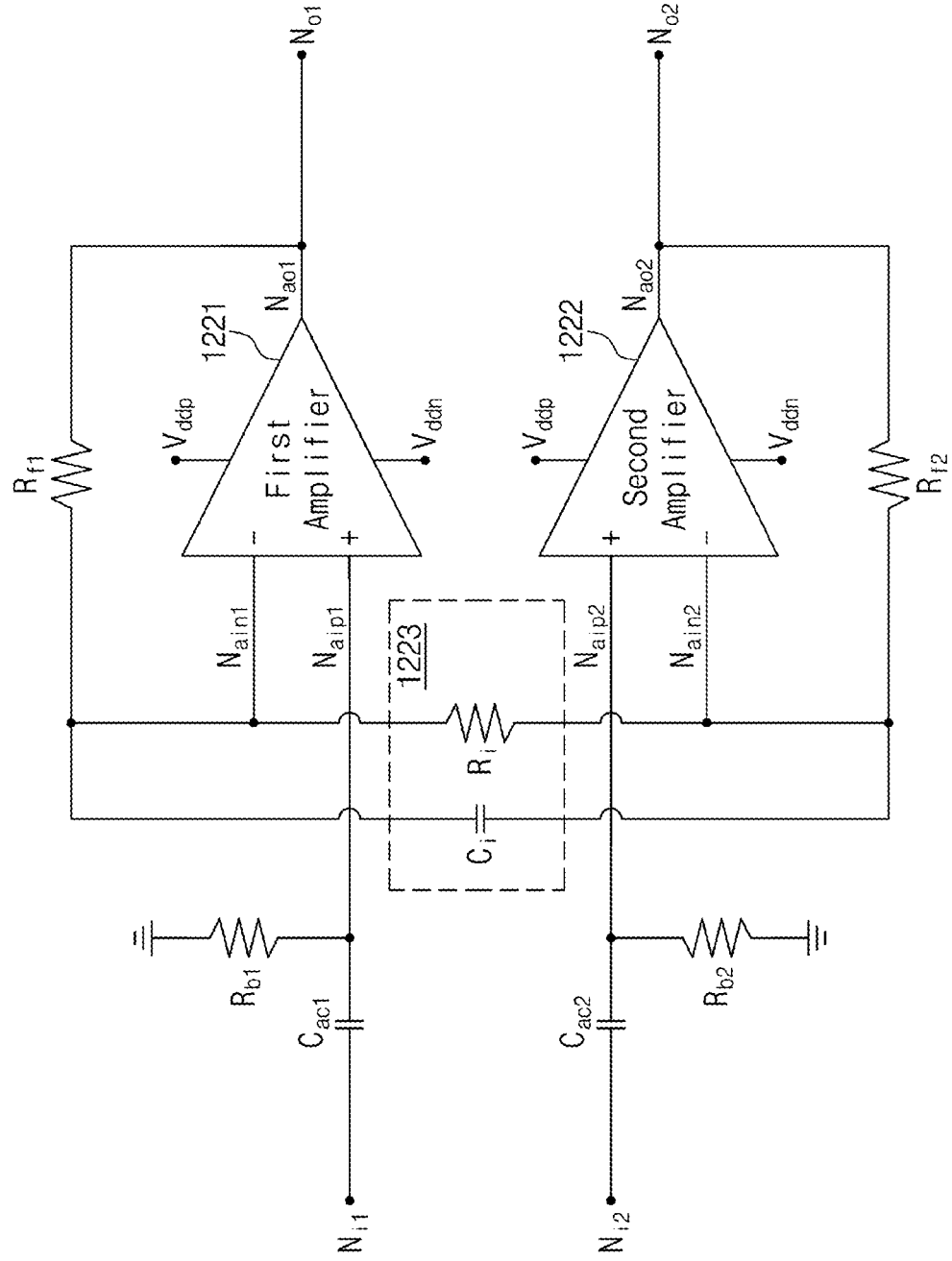
FIG. 6 is a diagram illustrating an analog amplifying unit according to an embodiment of the inventive concept.

FIG. 6 is a diagram illustrating an analog amplifying unit according to an embodiment of the inventive concept. Referring to FIG. 6, the analog amplifying unit 1220 may include a first amplifier 1221, a second amplifier 1222, and an input impedance 1223. The analog amplifying unit 1220 may have a first input terminal $N_{i1}$, a second input terminal $N_{i2}$, a first output terminal $N_{o1}$, and a second output terminal $N_{o2}$. The connection relationship among the terminals $N_{i1}$, $N_{o1}$, $N_{i2}$, and $N_{o2}$ in the analog amplifying unit 1220 will be described with reference to FIGS. 3 and 6.

The first input terminal $N_{i1}$ may be connected to the first receiving electrode 1211. The first differential signal DF1 may be received through the first input terminal $N_{i1}$. The second input terminal $N_{i2}$ may be connected to the second receiving electrode 1212. The second differential signal DF2 may be received through the second input terminal $N_{i2}$.

The first output terminal $N_{o1}$ may be connected to the signal restoring unit 1230. The first amplified differential signal ADF1 may be output through the first output terminal $N_{o1}$. The second output terminal $N_{o2}$ may be connected to the signal restoring unit 1230. The second amplified differential signal ADF2 may be output through the second output terminal $N_{o2}$.

The first amplifier 1221 may have a first non-inverting input terminal $N_{aip1}$, a first inverting input terminal $N_{ain1}$, and a first amplifying output terminal $N_{ao1}$. The first amplifier 1221 may be an operation amplifier OPAMP that operates by receiving a positive driving voltage $V_{ddp}$ and a negative driving voltage $V_{ddn}$.

The first amplifier 1221 may receive an input voltage through the first non-inverting input terminal $N_{aip1}$. In an embodiment, the first non-inverting input terminal $N_{aip1}$ may be connected to a first bias resistor $R_{b1}$. The first bias resistor $R_{b1}$ may be a device that provides a bias voltage to the first amplifier 1221.

In an embodiment, the first non-inverting input terminal $N_{aip1}$ may be connected to the first input terminal $N_{i1}$ through a first amplifier coupling capacitor $C_{ac1}$. The first amplifier coupling capacitor $C_{ac1}$ may be a device that passes an AC component and blocks a DC component in the first differential signal.

The first inverting input terminal $N_{ain1}$ may be connected to the second amplifier 1222 through the input impedance 1223. The first inverting input terminal $N_{ain1}$ may be connected to the first amplifying output terminal $N_{ao1}$ through a first feedback resistor $R_{f1}$.

The first amplified differential signal may be output from the first amplifying output terminal $N_{ao1}$. The first amplified differential signal may be a signal in which the first differential signal is amplified based on the input impedance 1223 and the first feedback resistor $R_{f1}$. The first amplified differential signal that is output from the first amplifying output terminal $N_{ao1}$ may be provided to the signal restoring unit 1230 through the first output terminal $N_{o1}$.

The second amplifier 1222 may have a second non-inverting input terminal $N_{aip2}$, a second inverting input terminal $N_{ain2}$, and a second amplifying output terminal $N_{ao2}$. The second amplifier 1222 may be an operation amplifier OPAMP that operates by receiving a positive driving voltage $V_{ddp}$ and a negative driving voltage $V_{ddn}$.

The second amplifier 1222 may receive an input voltage through the second non-inverting input terminal $N_{aip2}$. In an embodiment, the second non-inverting input terminal $N_{aip2}$ may be connected to a second bias resistor $R_{b2}$. The second bias resistor $R_{b2}$ may be a device that provides a bias voltage to the second amplifier 1222.

In an embodiment, the second non-inverting input terminal $N_{aip2}$ may be connected to the second input terminal $N_{i2}$ through a second amplifier coupling capacitor $C_{ac2}$. The second amplifier coupling capacitor $C_{ac2}$ may be a device that passes an AC component and blocks a DC component in the second differential signal.

The second inverting input terminal $N_{ain2}$ may be connected to the first amplifier 1221 through the input impedance 1223. The second inverting input terminal $N_{ain2}$ may be connected to the second amplifying output terminal $N_{ao2}$ through a second feedback resistor $R_{f2}$. The second differential signal may be amplified based on the input impedance 1223 and the second feedback resistor $R_{f2}$.

The second amplified differential signal may be output from the second amplifying output terminal $N_{ao2}$. The second amplified differential signal may be a signal in which the second differential signal is amplified based on the input impedance 1223 and the second feedback resistor $R_{f2}$. The second amplified differential signal that is output from the second amplifying output terminal $N_{ao2}$ may be provided to the signal restoring unit 1230 through the second output terminal $N_{o2}$.

The input impedance 1223 may be connected between the first inverting input terminal $N_{ain1}$ and the second inverting input terminal $N_{ain2}$. The input impedance 1223 may be a circuit that suppresses a low frequency band component and passes a high frequency band component. In an embodiment, the input impedance 1223 may be a circuit including an input resistor $R_i$ and an input capacitor $C_i$ that are connected in parallel with each other.

In an embodiment, in the analog amplifying unit 1220, a gain of the differential signal amplification in the high frequency band may be greater than a gain of the differential signal amplification in the low frequency band. The gain of the differential signal amplification may mean a value obtained by dividing a difference between the amplified differential signals by a difference between the differential signals.

For example, when the input impedance 1223 is a circuit including an input resistor $R_i$ and an input capacitor $C_i$ connected in parallel with each other, and the first feedback resistor Rf1 and the second feedback resistor Rf2 are the feedback resistors Rf having the same resistance value in ohms, the gain of the differential signal amplification in the analog amplifying unit 1220 may be expressed by the following equation.

$$GA_v = 1 + 2\frac{R_f}{Z} \qquad \text{[Equation 1]}$$

Referring to Equation 1, $GA_v$ may represent a gain of the differential signal amplification in the analog amplifying unit 1220 according to an embodiment of the inventive concept. $R_f$ is a magnitude value of a feedback resistor. Z is a magnitude value of an equivalent impedance in ohms associated with the input impedance including the input resistor $R_i$ and the input capacitor $C_i$ connected in parallel. Z may be a value that depends on a frequency. When Z is expressed as a function of frequency in Equation 1, $GA_v$ may be represented by an equation having a zero point.

Applying Equation 1, the gain $GA_v$ of the differential signal amplification in the low frequency band may be different from the gain $GA_v$ of the differential signal amplification in the high frequency band. The gain $GA_v$ of the differential signal amplification in the low frequency band may be approximated by the following equation.

$$GA_{vl} = 1 + 2\frac{R_f}{R_i} \qquad \text{[Equation 2]}$$

Referring to Equation 2, $GA_{vl}$ may represent a value in which the gain of the differential signal amplification is approximated at the low frequency band in the analog amplifying unit 1220 according to an embodiment of the inventive concept. $R_f$ is a magnitude value of a feedback resistor. $R_i$ is a magnitude value of an input resistor.

In an embodiment, the input capacitor $C_i$ may operate as an open circuit with respect to signals in the low frequency band. The input impedance including the input resistor $R_i$ and the input capacitor $C_i$ that are connected in parallel with each other may be approximated with the input resistor $R_i$. In this case, the input capacitor $C_i$ may be ignored.

Accordingly, Z in Equation 1 may be approximated with Equation 2 may be derived based on the approximated Z. That is, when Equation 2 is applied, the gain $GA_{vl}$ of the differential signal amplification approximated in the low frequency band may be provided. Meanwhile, the $GA_{vh}$ of the differential signal amplification in the high frequency band may be approximated by the following equation.

$$GA_{vh} = 1 + 2R_f 2\pi f C_i \qquad \text{[Equation 3]}$$

Referring to Equation 3, $GA_{vh}$ may represent a value in which the gain of the differential signal amplification is approximated in the high frequency band in the analog amplifying unit 1220 according to an embodiment of the inventive concept. $R_f$ is a magnitude value of a feedback resistor. f is a magnitude value of a frequency expressed in hertz. $C_i$ is a magnitude value of an input capacitor capacity.

In an exemplary embodiment, the input capacitor $C_i$ may operate as a short circuit with respect to signals in the high frequency band. The input impedance including the input resistor $R_i$ and the input capacitor $C_i$ that are connected in parallel with each other may be approximated with the input capacitor $C_i$. In this case, the input resistance $R_i$ may be ignored.

Accordingly, Z in Equation 1 may be approximated with an impedance value of the input capacitor $C_i$ with respect to a signal having a frequency f. Equation 3 may be derived based on the approximated Z. That is, when Equation 3 is applied, the gain $GA_{vh}$ of the differential signal amplification approximated in the high frequency band may be provided.

In an embodiment, the gain $GA_{vh}$ approximated at the high frequency band may be greater than the gain $GA_{vl}$ approximated at the low frequency band. Referring to Equations 2 and 3, unlike the gain $GA_{vl}$ of the differential signal amplification approximated at the low frequency band, the gain $GA_{vh}$ of the differential signal amplification approximated at the high frequency band may increase linearly in proportion to the frequency f.

As described above, according to an embodiment of the inventive concept, the analog amplifying unit 1220 may be provided in which the gain of the differential signal amplification at the high frequency band is greater than the gain of the differential signal amplification at the low frequency band. Accordingly, amplified differential signals in which a magnitude of a component of the high frequency band is similar to a magnitude of a component of the low frequency band may be obtained.

Figure 7:
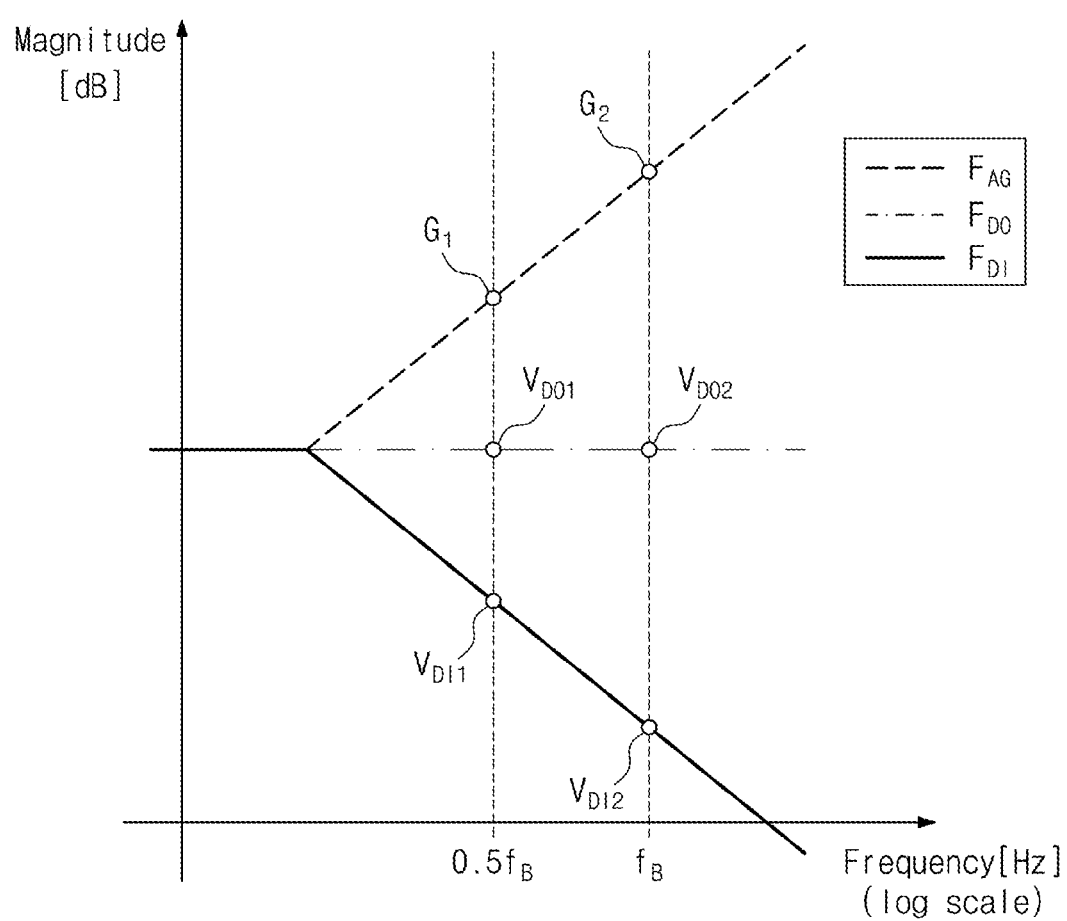
FIG. 7 is a graph illustrating voltage characteristics of an analog amplifying unit of FIG. 6 in a frequency domain.

FIG. 7 is a graph illustrating voltage characteristics of an analog amplifying unit of FIG. 6 in a frequency domain. Referring to FIG. 7, a differential amplifier input waveform $F_{-DI}$, a differential amplifier output waveform $F_{-Do}$, and an amplification gain waveform $F_{-AG}$ are illustrated in the frequency domain.

The differential amplifier input waveform $F_{-DI}$ is a waveform illustrating a magnitude of a difference between the first differential signal input to the analog amplifying unit 1220 through the first input terminal $N_{i1}$ and the second differential signal input to the analog amplifying unit 1220 through the second input terminal $N_{i2}$ in FIG. 6, in the frequency domain. The differential amplifier input waveform $F_{-DI}$ is depicted by a solid line.

Referring to FIG. 6 and the differential amplifier input waveform $F_{-DI}$, a magnitude $V_{DI1}$ of a first differential input voltage may be a magnitude of a difference between the first differential signal having a frequency 0.5 $f_B$ component that is half of the baseband frequency input to the first input terminal $N_{i1}$ and the second differential signal having a frequency 0.5 $f_B$ component that is half of the baseband frequency input to the second input terminal $N_{i2}$. A magnitude $V_{DI2}$ of a second differential input voltage may be a magnitude of a difference between the first differential signal having the baseband frequency $f_B$ component input to the first input terminal $N_{i1}$ and the second differential signal having the baseband frequency $f_B$ component input to the second input terminal $N_{i2}$.

In an embodiment, the differential signals input to the analog amplifying unit 1220 may be signals in which a magnitude of the high frequency component is less than a magnitude of the low frequency component, since the high frequency component is attenuated due to increasing of the rising time and the falling time and by transmitting the differential signals through the human body communication channel. For example, the magnitude $V_{DI2}$ of the second differential input voltage may be less than the magnitude $V_{DI1}$ of the first differential input voltage.

The amplification gain waveform $F_{-AG}$ is a waveform illustrating the gain $GA_v$ of the differential signal amplification in the analog amplifying unit 1220 of FIG. 6 in the frequency domain. The amplification gain waveform $F_{-AG}$ is depicted by a dashed line.

Referring to the amplification gain waveform $F_{-AG}$ and FIG. 6, a first amplification gain $G_{-1}$ may be a ratio at which the analog amplifying unit 1220 amplifies a differential signal having a frequency 0.5 $f_B$ component that is half of the baseband frequency. A second amplification gain $G_{-2}$ may be a ratio at which the analog amplifying unit 1220 amplifies a differential signal having a baseband frequency $f_B$ component.

In an embodiment, the analog amplifying unit 1220 may be provided in which the gain $GA_v$ of the differential signal amplification at the high frequency band is greater than the gain $GA_v$ of the differential signal amplification at the low frequency band. For example, the second amplification gain $G_{-2}$ may be greater than the first amplification gain $G_{-1}$.

In an embodiment, due to limitations of an amplifier device, the gain $GA_v$ of the differential signal amplification of the analog amplifying unit 1220 may be saturated in a high frequency range above a threshold frequency. Accordingly, although not illustrated in FIG. 7, the amplification gain waveform $F_{-AG}$ may represent a gain $GA_v$ of the differential signal amplification that does not linearly increase in the range above the threshold frequency.

The differential amplifier output waveform $F_{-DO}$ is a waveform illustrating a magnitude of a difference between the first amplified differential signal output through the first output terminal $N_{o1}$ and the second amplified differential signal output through the second output terminal $N_{o2}$ in FIG. 6 in the frequency domain. The differential amplifier output waveform $F_{-DO}$ is depicted by a dash-single dotted line.

Referring to the differential amplifier output waveform $F_{-DO}$ and FIG. 6, a magnitude $V_{DO1}$ of a first differential output voltage may be a magnitude of a difference between the first amplified differential signal having a frequency 0.5 $f_B$ component that is half of the baseband frequency output from the first output terminal $N_{o1}$ and the second amplified differential signal having a frequency 0.5 $f_B$ component that is half of the baseband frequency output from the second output terminal $N_{o2}$.

A magnitude $V_{DO2}$ of a second differential output voltage may be a magnitude of a difference between the first amplified differential signal having a baseband frequency $f_B$ component output from the first output terminal $N_{o1}$ and second amplified differential signal having baseband frequency $f_B$ component output from second output terminal $N_{o2}$.

In an embodiment, the amplified differential signals that are output from the analog amplifying unit 1220 may be signals in which a gain of an attenuated high frequency component is compensated for. The gain $GA_v$ of the differential signal amplification in the analog amplifying unit 1220 may compensate for the gain of the attenuated high frequency component.

For example, a difference between the magnitude $V_{DO1}$ of the first differential output voltage and the magnitude $V_{DI1}$ of the first differential input voltage may be equal to a difference between the magnitude of the first amplification gain $G_{-1}$ and the magnitude $V_{DO1}$ of the first differential output voltage. In addition, a difference between the magnitude $V_{DO2}$ of the second differential output voltage and the magnitude $V_{DI2}$ of the second differential input voltage may be equal to a difference between the second amplification gain $G_{-2}$ and the magnitude $V_{DO2}$ of the second differential output voltage.

In an embodiment, the amplified differential signals that are output from the analog amplifying unit 1220 may be signals in which the magnitude of the high frequency component may be similar to the magnitude of the low frequency component. For example, the magnitude $V_{DO1}$ of the first differential output voltage may be similar to the magnitude $V_{DO2}$ of the second differential output voltage.

As described above, according to an embodiment of the inventive concept, by compensating the gain of the high frequency component attenuated as the rising time and the falling time are increased and the gain of the high frequency component attenuated as the differential signals are transmitted through the human body communication channel, an analog amplifying unit that outputs the amplified differential signals in which a magnitudes of a high frequency component is similar to a magnitudes of a low frequency component may be provided.

Figure 8:
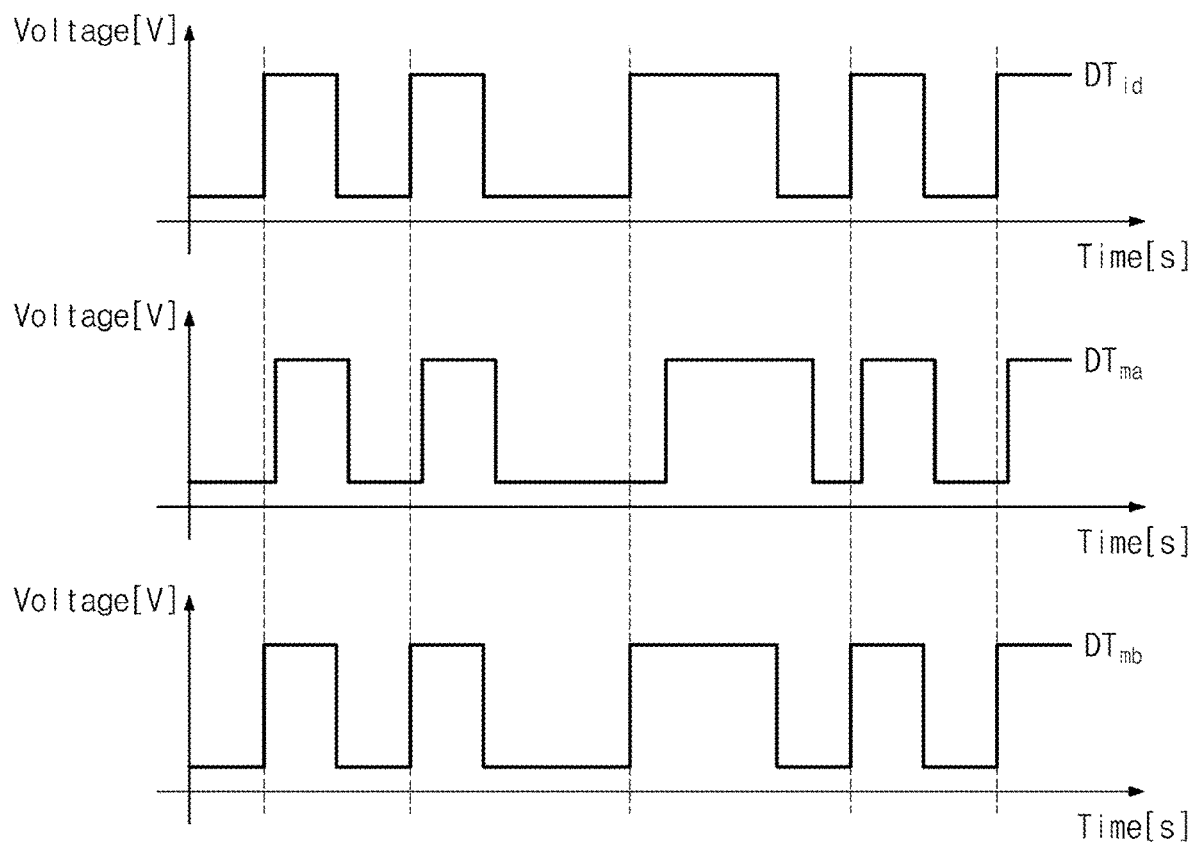
FIG. 8 is a graph illustrating a data signal to be restored in a time domain according to an embodiment of the inventive concept.

FIG. 8 is a graph illustrating a data signal to be restored in a time domain according to an embodiment of the inventive concept. Referring to FIG. 8, an ideal data signal $DT_{id}$, a data signal $DT_{ma}$ according to an embodiment of FIG. 3, and a data signal $DT_{mb}$ according to an embodiment of FIG. 6 are illustrated in a time domain. Since the characteristics of the ideal data signal $DT_{id}$ and the data signal $DT_{ma}$ according to an embodiment of FIG. 3 are similar to those described in the data signal graph $G_{DT}$ of FIG. 5, additional description thereof will be omitted to avoid redundancy.

The data signal $DT_{mb}$ according to an embodiment of FIG. 6 may be a restored data signal based on the amplified differential signals that are output from the analog amplifying unit 1220 of FIG. 6. In this case, the amplified differential signals may be signals in which a magnitude of the high frequency component is similar to a magnitude of the low frequency component as the gain of the attenuated high frequency component is compensated for.

In an embodiment, the data signal $DT_{mb}$ according to an embodiment of FIG. 6 may be a signal having a reduced bit error than the data signal $DT_{ma}$ according to an embodiment of FIG. 3. The data signal $DT_{mb}$ according to an embodiment of FIG. 6 may have a bit width similar to that of the ideal data signal $DT_{id}$.

In an embodiment, the image inside body, which is restored based on a data signal (e.g., $DT_{mb}$) having a bit width similar to the ideal data signal $DT_{id}$, may be an image having better image quality. For example, the restored image internal body, based on the data signal $DT_{mb}$ according to an embodiment of FIG. 6 may be an image having better image quality than the restored image inside body, based on the data signal $DT_{ma}$ according an embodiment of FIG. 3.

As described above, according to an embodiment of the inventive concept, an analog amplifying unit that compensates for the gain of the attenuated high frequency component may be provided. A data signal (e.g., $DT_{mb}$), which is restored based on differential signals in which a gain of the attenuated high frequency component is compensated for may be a signal in which bit width variation is suppressed.

Figure 9:
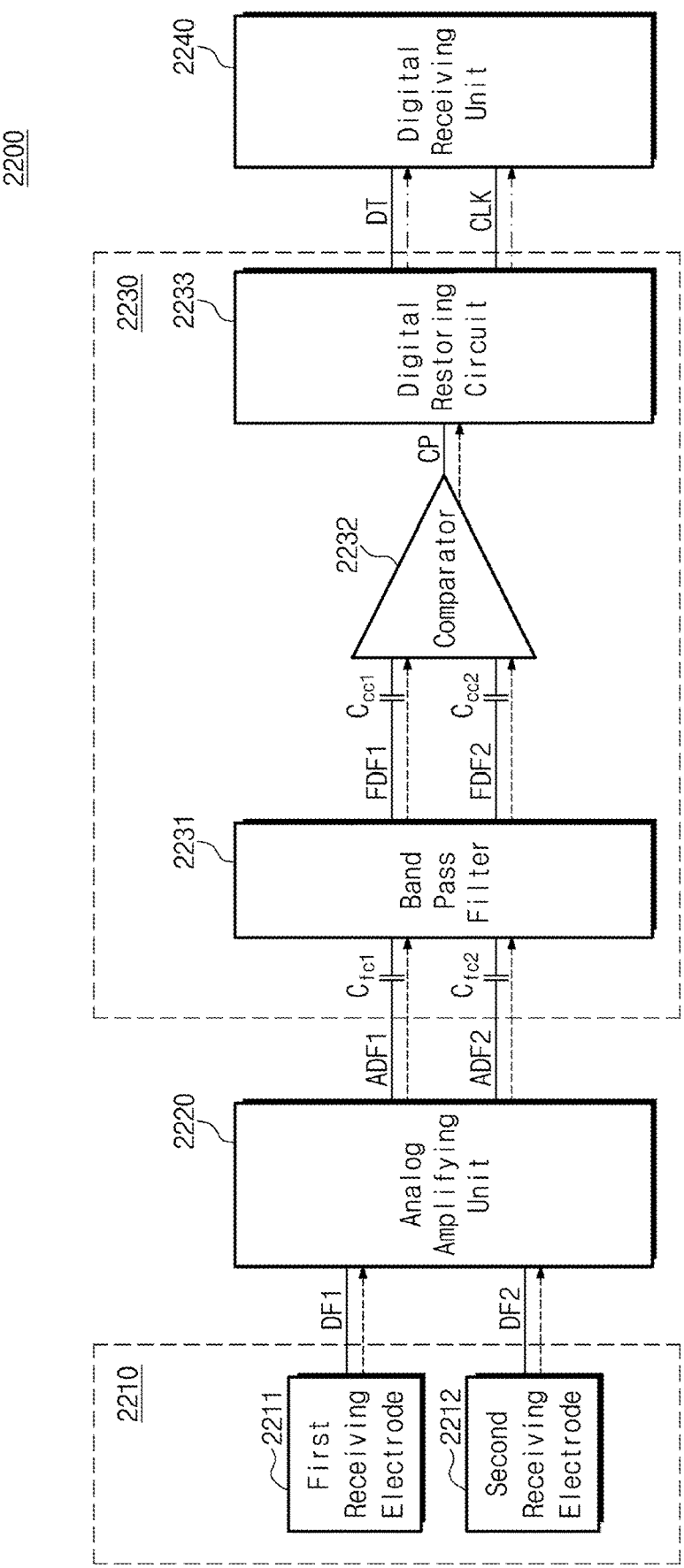
FIG. 9 is a diagram illustrating a capsule endoscope image receiver of FIG. 1.

FIG. 9 is a diagram illustrating a capsule endoscope image receiver of FIG. 1. Referring to FIG. 9, a capsule endoscope image receiver 2200 may include a receiving electrode unit 2210, an analog amplifying unit 2220, a signal restoring unit 2230, and a digital receiving unit 2240. Since the characteristics of the receiving electrode unit 2210, the analog amplifying unit 2220, and the digital receiving unit 2240 are similar to those described in FIG. 3, additional description thereof will be omitted to avoid redundancy.

The signal restoring unit 2230 may include a band pass filter 2231, a comparator 2232, and a digital restoring circuit 2233. The band pass filter 2231 may receive the first amplified differential signal ADF1 from the analog amplifying unit 2220 through a first filter coupling capacitor $C_{fc1}$. The band pass filter 2231 may receive the second amplified differential signal ADF2 from the analog amplifying unit 2220 through a second filter coupling capacitor $C_{fc2}$.

The first filter coupling capacitor $C_{fc1}$ may be a device that passes an AC component and blocks a DC component of the first amplified differential signal ADF1. The second filter coupling capacitor $C_{fc2}$ may be a device that passes the AC component and blocks the DC component of the second amplified differential signal ADF2.

The comparator 2232 may receive the first filtered differential signal FDF1 from the band pass filter 2231 through a first comparator coupling capacitor $C_{cc1}$. The comparator 2232 may receive the second filtered differential signal FDF2 from the band pass filter 2231 through a second comparator coupling capacitor $C_{cc2}$.

The first comparator coupling capacitor $C_{cc1}$ may be a device that passes an AC component and blocks a DC component of the first filtered differential signal FDF1. The second comparator coupling capacitor $C_{cc2}$ may be a device that passes the AC component and blocks the DC component of the second filtered differential signal FDF2.

As described above, according to an embodiment of the inventive concept, the band pass filter 2231 may be provided that receives the amplified differential signals ADF1 and ADF2 through the filter coupling capacitors $C_{fc1}$ and $C_{fc2}$ that block the DC component. In addition, the comparator 2232 may be provided that receives the differential signals FDF1 and FDF2 filtered through the comparator coupling capacitors $C_{cc1}$ and $C_{cc2}$ that block the DC component.

Figure 10A:
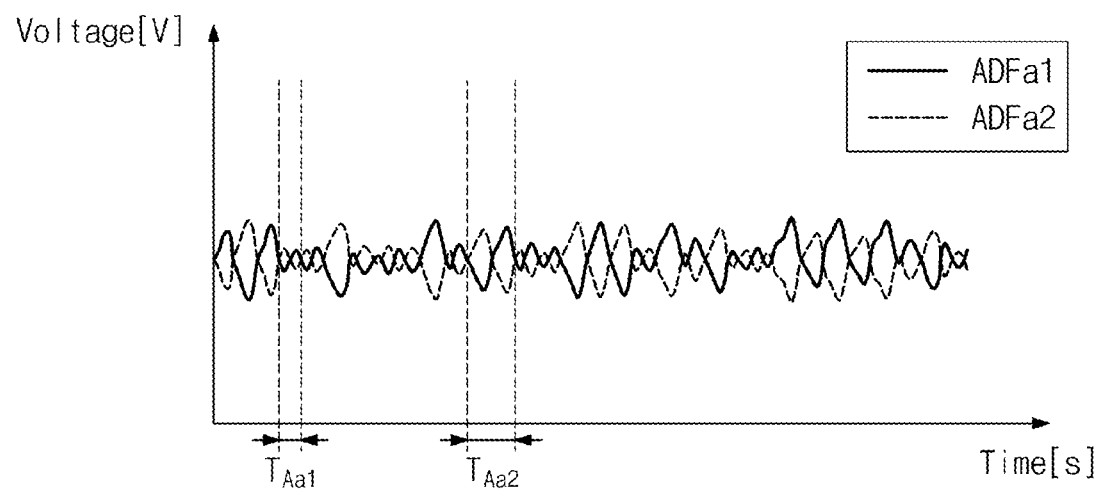
FIG. 10A is a graph illustrating an exemplary measurement of amplified differential signals according to an embodiment of the inventive concept.

FIG. 10A is a graph illustrating an exemplary measurement of amplified differential signals according to an embodiment of the inventive concept. Referring to FIG. 10A, waveforms measuring the first amplified differential signal and the second amplified differential signal are illustrated. The first amplified differential signal and the second amplified differential signal are output from an analog amplifying unit (e.g., the analog amplifying unit of FIG. 3) that has a differential signal amplification gain in the high frequency band similar to a differential signal amplification gain in the low frequency band.

A first measurement waveform ADFa1 according to an embodiment of FIG. 3 may be a waveform of the first amplified differential signal ADF1 of FIG. 3. The first measurement waveform ADFa1 according to an embodiment of FIG. 3 is depicted by a solid line. A second measurement waveform ADFa2 according to an embodiment of FIG. 3 may be a waveform of the second amplified differential signal ADF2 of FIG. 3. The second measurement waveform ADFa2 according to an embodiment of FIG. 3 is depicted by a dashed line.

The measurement waveforms ADFa1 and ADFa2 according to an embodiment of FIG. 3 may have waveforms of a high frequency period $T_{Aa1}$ according to an embodiment of FIG. 3 and waveforms of a low frequency period $T_{Aa2}$ according to an embodiment of FIG. 3. In an embodiment, a voltage difference between the measurement waveforms ADFa1 and ADFa2 according to an embodiment of FIG. 3 having the high frequency period $T_{Aa1}$ according to an embodiment of FIG. 3 may be less than a voltage difference between the measurement waveforms ADFa1 and ADFa2 according to an embodiment of FIG. 3 having the low frequency period $T_{Aa2}$ according to an embodiment of FIG. 3.

As described above, according to an embodiment of the inventive concept, the amplified differential signals that are measured by an analog amplifying unit having a differential signal amplification gain in the high frequency band similar to the differential signal amplification gain in the low frequency band may have a magnitude of the high frequency component less than that of the low frequency component.

Figure 10B:
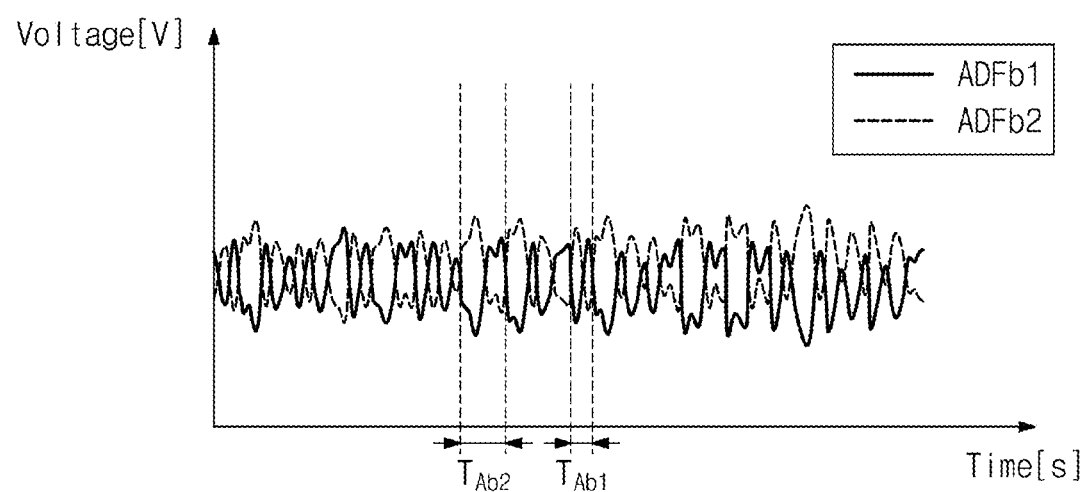
FIG. 10B is a graph illustrating an exemplary measurement of amplified differential signals according to an embodiment of the inventive concept.

FIG. 10B is a graph illustrating an exemplary measurement of amplified differential signals according to an embodiment of the inventive concept. Referring to FIG. 10B, waveforms measuring the first amplified differential signal and the second amplified differential signal are illustrated. The first amplified differential signal and the second amplified differential signal are output from an analog amplifying unit (e.g., the analog amplifying unit of FIG. 6) that has a differential signal amplification gain in the high frequency band greater than a differential signal amplification gain in the low frequency band.

A first measurement waveform ADFb1 according to an embodiment of FIG. 6 may be a waveform obtained by measuring the first amplified differential signal output from the analog amplifying unit of FIG. 6. The first measurement waveform ADFb1 according to an embodiment of FIG. 6 is depicted by a solid line. A second measurement waveform ADFb2 according to an embodiment of FIG. 6 may be a waveform obtained by measuring the second amplified differential signal output from the analog amplifying unit of FIG. 6. The second measurement waveform ADFb2 according to an embodiment of FIG. 6 is depicted by a dashed line.

The measurement waveforms ADFb1 and ADFb2 according to an embodiment of FIG. 6 may have waveforms of a high frequency period $T_{Aa1}$ according to an embodiment of FIG. 6 and waveforms of a low frequency period $T_{Aa2}$ according to an embodiment of FIG. 6. In an embodiment, a voltage difference between the measurement waveforms ADFb1 and ADFb2 according to an embodiment of FIG. 6 having the high frequency period $T_{Aa1}$ according to an embodiment of FIG. 6 may be similar to a voltage difference between the measurement waveforms ADFb1 and ADFb2 according to an embodiment of FIG. 6 having the low frequency period $T_{Aa2}$ according to an embodiment of FIG. 6.

As described above, according to an embodiment of the inventive concept, the amplified differential signals that are measured by an analog amplifying unit having a differential signal amplification gain in the high frequency band greater than the differential signal amplification gain in the low frequency band may have a magnitude of the high frequency component similar to that of the low frequency component.

According to an embodiment of the inventive concept, a capsule endoscope image receiver and a capsule endoscope device including the same are provided which compensate for the attenuation caused by the signal transmission and reception of a capsule endoscope.

In addition, by compensating a gain of a attenuated high frequency band signal, a capsule endoscope image receiver and a capsule endoscope device including the same are provided, thereby restoring an endoscope image signal with suppressed error and bit width variation.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments. Therefore, the scope of the inventive concept is not limited to the described embodiments but should be defined by the claims and their equivalents.

What is claimed is:

1. A capsule endoscope image receiver comprising:
    a receiving electrode unit configured to receive first and second differential signals from a capsule endoscope image transmitter through a human body communication channel;
    an analog amplifying unit configured to receive the first and second differential signals from the receiving electrode unit, and to output first and second amplified differential signals, based on the received first and second differential signals; and
    a signal restoring unit configured to receive the first and second amplified differential signals from the analog amplifying unit, and to restore image information, based on the received first and second amplified differential signals, and
    wherein the analog amplifying unit includes:
    a first amplifier configured to output the first amplified differential signal, based on the first differential signal;
    a second amplifier configured to output the second amplified differential signal, based on the second differential signal; and
    an input impedance connected between a first inverting input terminal of the first amplifier and a second inverting input terminal of the second amplifier, and configured to obtain a gain of differential signal amplification in which a high frequency component of the first and second amplified differential signals is greater than a low frequency component.

2. The capsule endoscope image receiver of claim 1, wherein the input impedance includes an input resistor and an input capacitor that are connected in parallel between the first inverting input terminal and the second inverting input terminal.

3. The capsule endoscope image receiver of claim 2, wherein the analog amplifying unit further includes first and second feedback resistors, wherein the first feedback resistor is connected between a first output terminal of the first amplifier and the first inverting input terminal, and wherein the second feedback resistor is connected between a second output terminal of the second amplifier and the second inverting input terminal.

4. The capsule endoscope image receiver of claim 3, wherein a difference between the first and second amplified differential signals has a magnitude that is greater than a difference between the first and second differential signals by the gain of the differential signal amplification, and wherein the gain of the differential signal amplification is determined based on the first feedback resistor, the second feedback resistor, and the input impedance.

5. The capsule endoscope image receiver of claim 1, wherein the receiving electrode unit includes a first receiving electrode configured to receive the first differential signal and a second receiving electrode configured to receive the second differential signal,
wherein the first amplifier receives the first differential signal from the first receiving electrode through a first amplifier coupling capacitor, and
wherein the second amplifier receives the second differential signal from the second receiving electrode through a second amplifier coupling capacitor.

6. The capsule endoscope image receiver of claim 1, wherein the signal restoring unit includes a band pass filter configured to block noise of the first and second amplified differential signals that are received from the analog amplifying unit.

7. The capsule endoscope image receiver of claim 6, wherein the band pass filter receives the first amplified differential signal from a first output terminal of the first amplifier through a first filter coupling capacitor, and
wherein the band pass filter receives the second amplified differential signal from a second output terminal of the second amplifier through a second filter coupling capacitor.

8. The capsule endoscope image receiver of claim 1, wherein the signal restoring unit includes a digital restoring circuit that restores a data signal and a clock signal, based on the first and second amplified differential signals,
wherein the data signal includes the image information, and
wherein the clock signal includes clock signal information of the capsule endoscope image transmitter.

9. The capsule endoscope image receiver of claim 8, further comprising
a digital receiving unit configured to receive the data signal and the clock signal from the digital restoring circuit and to restore an image captured by the capsule endoscope image transmitter, based on the received data signal and the received clock signal.

10. The capsule endoscope image receiver of claim 9, wherein the signal restoring unit further includes:
a band pass filter configured to block noise of the first and second amplified differential signals received from the analog amplifying unit, and to output first and second filtered differential signals from which the noise is blocked; and
a comparator configured to receive the first and second filtered differential signals, and to output a comparison signal restored to a size that the digital receiving unit is able to process to the digital restoring circuit, based on the received first and second filtered differential signals.

11. The capsule endoscope image receiver of claim 10, wherein the comparator receives the first filtered differential signal from the band pass filter through a first comparator coupling capacitor and receives the second filtered differential signal from the band pass filter through a second comparator coupling capacitor.

12. A capsule endoscope device comprising:
a capsule endoscope image transmitter configured to capture an image of an inside of a body, to obtain image information based on the captured image, and to output first and second differential signals including the obtained image information, respectively; and
a capsule endoscope image receiver,
wherein the capsule endoscope image receiver includes:
a receiving electrode unit configured to receive the first and second differential signals from the capsule endoscope image transmitter through a human body communication channel;
an analog amplifying unit configured to receive the first and second differential signals from the receiving electrode unit, and to output first and second amplified differential signals, based on the received first and second differential signals; and
a signal restoring unit configured to receive the first and second amplified differential signals from the analog amplifying unit, and to restore the image information, based on the received first and second amplified differential signals, and
wherein the analog amplifying unit includes:
a first amplifier configured to output the first amplified differential signal, based on the first differential signal;
a second amplifier configured to output the second amplified differential signal, based on the second differential signal; and
an input impedance connected between a first inverting input terminal of the first amplifier and a second inverting input terminal of the second amplifier, and configured to obtain a gain of differential signal amplification in which a high frequency component of the first and second amplified differential signals is greater than a low frequency component.

13. The capsule endoscope device of claim 12, wherein the receiving electrode unit includes a first receiving electrode configured to receive the first differential signal and a second receiving electrode configured to receive the second differential signal, and
wherein the capsule endoscope image transmitter includes:
an image sensor configured to capture the image inside the body and to output an image signal including the obtained image information;
a signal driver configured to receive the image signal from the image sensor and to output the first and second differential signals, based on the image signal;
a first transmitting electrode configured to receive the first differential signal from the signal driver and to output the first differential signal to the first receiving electrode through the human body communication channel; and
a second transmitting electrode configured to receive the second differential signal from the signal driver and to output the second differential signal to the second receiving electrode through the human body communication channel.

14. The capsule endoscope device of claim 13, wherein the first transmitting electrode receives the first differential signal from the signal driver through a first current limitation resistor, and wherein the second transmitting electrode receives the second differential signal from the signal driver through a second current limitation resistor.

\* \* \* \* \*